United States Patent [19]

Stevens et al.

[11] Patent Number: 4,831,060

[45] Date of Patent: * May 16, 1989

[54] MIXED ALCOHOLS PRODUCTION FROM SYNGAS

[75] Inventors: Rex R. Stevens, Midland; Mark M. Conway, Sanford, both of Mich.

[73] Assignee: The Dow Chemical Company, Midland, Mich.

[ * ] Notice: The portion of the term of this patent subsequent to Jun. 21, 2005 has been disclaimed.

[21] Appl. No.: 202,754

[22] Filed: Jun. 6, 1988

Related U.S. Application Data

[60] Division of Ser. No. 942,933, Dec. 17, 1986, Pat. No. 4,752,623, which is a continuation of Ser. No. 779,906, Sep. 25, 1985, abandoned, which is a continuation-in-part of Ser. No. 636,000, Jul. 30, 1984, abandoned.

[51] Int. Cl.$^4$ .............................................. C07L 27/06
[52] U.S. Cl. .................................... 518/714; 518/728; 518/717; 502/219; 502/220
[58] Field of Search ........................................ 518/214

[56] References Cited

U.S. PATENT DOCUMENTS

| | | |
|---|---|---|
| 1,201,850 | 10/1916 | Mittasch et al. . |
| 1,558,559 | 10/1925 | Mittasch et al. . |
| 1,859,244 | 5/1932 | Patart . |
| 2,490,488 | 12/1949 | Stewart . |
| 2,539,414 | 1/1951 | Frankenburg . |
| 2,821,537 | 1/1958 | Rottig . |
| 2,960,518 | 11/1960 | Peters . |
| 3,842,113 | 10/1974 | Ichikawa et al. . |
| 3,842,121 | 10/1974 | Ichikawa . |
| 3,850,840 | 2/1972 | Aldridge et al. . |
| 3,928,000 | 12/1975 | Child et al. . |
| 4,096,164 | 6/1978 | Ellgen et al. . |
| 4,151,190 | 4/1979 | Murchison et al. . |
| 4,151,191 | 4/1979 | Happel et al. . |
| 4,168,276 | 9/1979 | Finch . |
| 4,177,202 | 12/1979 | Chang et al. . |
| 4,199,522 | 4/1980 | Murchison et al. . |
| 4,260,553 | 4/1981 | Happel et al. . |
| 4,261,864 | 4/1981 | Hargis . |
| 4,298,354 | 11/1981 | Hardman et al. . |
| 4,380,589 | 4/1983 | Murchison et al. . |
| 4,405,815 | 9/1983 | Keim et al. . |
| 4,440,668 | 4/1984 | Chang et al. . |
| 4,451,579 | 5/1984 | Lemanski et al. . |
| 4,459,369 | 7/1984 | Passariello . |
| 4,478,954 | 10/1984 | Connolly et al. . |
| 4,511,674 | 4/1985 | Pedersen et al. . |
| 4,513,096 | 4/1985 | Connolly et al. . |
| 4,513,100 | 4/1985 | Fattore et al. . |
| 4,544,673 | 10/1985 | Lemanski et al. . |
| 4,607,055 | 8/1986 | Grazioso et al. . |
| 4,607,056 | 8/1986 | Grazioso et al. . |
| 4,616,040 | 10/1986 | Grazioso et al. . |
| 4,661,525 | 4/1987 | Grazioso et al. . |
| 4,675,344 | 6/1987 | Conway et al. . |
| 4,749,724 | 6/1988 | Quarderer et al. . |
| 4,752,622 | 6/1988 | Stevens . |
| 4,752,623 | 6/1988 | Stevens et al. . |

FOREIGN PATENT DOCUMENTS

| | | |
|---|---|---|
| 251483 | 7/1925 | Canada . |
| 119609 | 9/1984 | European Pat. Off. . |
| 149255 | 7/1985 | European Pat. Off. . |
| 149256 | 7/1985 | European Pat. Off. . |
| 1058797 | 3/1954 | France . |
| 170023 | 9/1984 | Japan . |
| 254760 | 7/1926 | United Kingdom . |
| 1501892 | 2/1978 | United Kingdom . |
| 2065490 | 7/1981 | United Kingdom . |
| 2151616 | 7/1985 | United Kingdom . |

OTHER PUBLICATIONS

British Coal Corp., Letter to the EPO, Dated Jul. 6, 1987.
Anderson, R. B. et al., "Fischer-Tropsch Synthesis", Engineering and Process Development, *Industrial & Engineering Chemistry*, vol. 44, No. 2, pp. 391–401 (1952).
Anderson, R. B. et al., "Synthesis of Alochols by Hydrogenation of Carbon Monoxide", Industrial and Engineering Chemistry, vol. 44, No. 10, pp. 2418, 2424 (1952).
*A Critical Analysis of Recent Advances in CO–$H_2$ Catalysis*, Prepared by Catalytica Assoc., Inc., Santa Clara, CA 95051, Multiclient Study No. 1124, June, 1980 (excerpted).
Tatsumi et al., *Chemistry Letters*, Chemical Society of Japan(5), pp. 685–688 (1984).
Diffenbach, R. A. et al., *Synthesis Gas Conversion to Liquid Fuels Using Promoted Fused Iron Catalysts*, DOE/PETC/TR-81/3 (September, 1981).
Greene, *C.E.P.* (August, 1982), pp. 46–51.
Kummer, J. T. et al., vol. 73, pp. 564–569 (February, 1951).
Kummer, J. T. et al., vol. 75, pp. 5177–5183 (Nov. 5, 1953).

*Primary Examiner*—Howard T. Mars
*Attorney, Agent, or Firm*—Charles J. Enright

[57] ABSTRACT

Mixed alcohols are produced from carbon monoxide and hydrogen gases using an easily prepared catalyst/co-catalyst metal catalyst. The catalyst metals are molybdenum, tungsten or rhenium. The co-catalyst metals are cobalt, nickel or iron. The catalyst is promoted with a Fischer-Tropsch promoter like an alkali or alkaline earth series metal or a smaller amount of thorium and is further treated by sulfiding. The composition of the mixed alcohols fraction can be selected by selecting the extent of intimate contact among the catalytic components.

12 Claims, No Drawings

MIXED ALCOHOLS PRODUCTION FROM SYNGAS

CROSS-REFERENCE TO RELATED APPLICATION

This is a divisional of application Ser. No. 942,933, filed Dec. 17, 1986, which is now issued as U.S. Pat. No. 4,752,623 which is a continuation of Ser. No. 779,906, filed Sept. 25, 1985 which is now abandoned which is a continuation-in-part of Ser. No. 636,000, filed July 30, 1984 which is now abandoned.

FIELD OF THE INVENTION

This invention relates to a process for producing mixed alcohols from synthesis gas. It also relates to a catalyst composition.

BACKGROUND OF THE INVENTION

Almost as old as the Fischer-Tropsch process for making hydrocarbons is the Fischer-Tropsch process for making alcohols. The reaction is carried out by passing a mixture of carbon monoxide and hydrogen over a catalyst for the hydrogenation of the carbon monoxide. A typical review article is R. B. Anderson et al., *Industrial and Engineering Chemistry*, Vol. 44, No. 10, pp. 2418–2424 (incorporated herein by reference). This paper lists a number of catalysts containing zinc, copper, chromium, manganese, thorium, iron, occasionally promoted with alkali or other materials for making various alcohols. The authors state that ethyl alcohol is a major constituent, the yield of methanol is usually very small and a tentative summary of factors favoring the production of alcohols is high pressure, low temperature, high space velocity, high recycle ratio and carbon monox- ide-rich synthesis gas.

Molybdenum, tungsten and rhenium are known to be catalytic for the Fischer-Tropsch process. Murchison et al. in U.S. Pat. No. 4,151,190 (1979) and U.S. Pat. No. 4,199,522 (1980) (both incorporated herein by reference). The references describe some Fischer-Tropsch catalysts but do not teach that the catalyst is useful for making commercially significant quantities of alcohols. These references note that hydrogen sulfide affects the activity of the catalyst.

Pedersen et al., British Patent Publication No. 2,065,291 (incorporated herein by reference), disclose a process for making $C_2$ hydrocarbons from $H_2/CO$ using a catalyst comprising a group VB and/or VIB element in combination with an iron group metal as free metals, oxides or sulfides on a porous oxidic support. The authors note that the presence of $H_2S$ alters the activity and selectivity of their process.

Chang et al., U.S. Pat. No. 4,177,202 (incorporated herein by reference), disclose a process for making hydrocarbons from $H_2/CO$ over a molybdena and optionally cobalt or vanadium catalyst. Selectivity to ethane is enhanced by presence of hydrogen sulfide in the feed.

Stewart, U.S. Pat. No. 2,490,488 (incorporated herein by reference), discloses that molybdenum sulfide methanation catalysts acquire Fischer-Tropsch activity when promoted with an alkaline compound of an alkali metal. The example of the invention shows a 30 percent selectivity to $C_3+$ hydrocarbons and oxygenates. Of this 30 percent, no more than 44 percent boils near or above 65° C., the boiling point of methanol. Accordingly, the maximum possible alcohol selectivity is no more than 13.2 percent (44 percent of 30 percent).

U.S. Pat. No. 2,539,414 (incorporated herein by reference) describes a Fischer-Tropsch process with molybdenum carbide catalysts. It teaches that the catalyst may be used to form oxygenates and at column 3, lines 66-71 teaches that one might get alcohols or hydrocarbons by varying the conditions.

Morgan et al., *J. Soc. Chem. Ind.*, 51, pp. 1T–7T (Jan. 8, 1932), describe a process for making alcohols with chromium/manganese oxide catalysts promoted with alkali.

A number of references teach production of alcohols using rhodium catalysts. Some of these contain molybdenum as an optional ingredient. Ellgen et al., U.S. Pat. No. 4,014,913 (incorporated herein by reference) discloses a catalyst containing rhodium and thorium or uranium and iron or molybdenum or tungsten for the production of ethanol. Ellgen et al., U.S. Pat. No. 4,096,164 (incorporated in combination with molybdenum or tungsten. Example A discloses that use of a molybdenum-on-silica catalyst yielded 4.4 percent oxygenates. Ball, EPO application No. 81-33,212 (Chemical Abstracts 96:51,800a) (incorporated herein by reference), discloses a similar process using rhodium in combination with one or more of a long list of metals which includes molybdenum.

Hardman et al., EPO application No. 79-5,492 (Chemical Abstracts 92:166,257b) (incorporated herein by reference), disclose the production of alcohols using a 4-component catalyst. The first component is copper; the second is thorium; the third is an alkali metal promoter; and the fourth is a long list of metals one of which is molybdenum. Diffenbach et al., Chemical Abstracts 96:106,913x, disclose a nitrided iron catalyst which is promoted with molybdenum for making alcohols from synthesis gas.

Kinkade (Union Carbide), European Patent Application No. 84116467.6 (published July 24, 1985, Publ. No. 149,255) (incorporated herein by reference), discloses that $C_{1-5}$ n-alcohols are substantially produced with a catalyst consisting essentially of molybdenum sulfide and an alkali metal compound. The gas hourly space velocity (i.e., GHSV) must be about 3000 hour$^{-1}$ or above. Variations in the GHSV, temperature, pressure and alkali metal compound are disclosed to affect the alcohols' selectivity.

Quarderer et al. (Dow Chemical), European Patent Application No. 84102932.5 (published Sept. 26, 1984, Publ. No. 119,609) (incorporated herein by reference), discloses that alcohols which boil in the range of motor gasoline are made at good selectivities from syngas with an optionally supported Mo/W/Re and alkali/alkaline earth element catalyst. In certain preferred embodiments, it is disclosed that Mo/W/Re sulfides, carbon supports (when the catalyst is supported) are favored, and it is preferred to exclude cobalt.

It is known to dope certain catalysts with cobalt. However, no resultant selectivities to certain alcohols are taught to be incrementally and simply varied therewith. See, Shultz et al., U.S. Bureau of Mines, R.I. 6974 (incorporated herein by reference).

To make a commercially significant alcohol process, one must use a catalyst and conditions which are highly efficient. To be efficient, the catalyst must yield a high weight ratio of product per unit weight of catalyst in a given period of time. The catalyst must be stable and active for long periods of time between regenerations.

This may be particularly difficult to accomplish when the $H_2/CO$ ratio of the feed gas is low, such as less than 2 to 1. Ideally the catalyst will be sulfur tolerant and will have a high selectivity to a commercial product to avoid purification or removal and disposal of by-products and to avoid separation into two or more product streams.

When the mixed alcohols product is to be used as a fuel replacement or a fuel additive, it may be desirable that the ratio of $C_1$ to $C_2+$ alcohols be no greater than a certain amount. Excessive methanol is generally considered an unattractive additive to gasolines. Methanol may decrease drivability and may increase corrosion in the fuel system and may cause phase separation when used in excessive quantities. These problems may be alleviated by blending methanol with higher alcohols.

Accordingly, one may wish to synthesize mixed alcohols with no more than a certain amount of methanol in the blend. Or in a similar fashion, one may wish to select the ratio of $C_1$ to $C_2+$ alcohols in mixed alcohols so that methanol may be purchased and blended into the mixed alcohols to give the maximum acceptable $C_1$ to $C_2+$ alcohols ratio.

A problem in the art to be solved is enhancing the efficiency of the overall process to include catalyst preparation. Another problem to be solved is how to simply and efficiently select the ratio of $C_1$ to $C_2+$ alcohols without exclusively relying on distilling of the product stream, varying the sulfur content of the feed stream or without relying on mixing of various discrete catalysts. Another problem to be solved is the conservation of energy in the conversion into $C_2+$ alcohols. Another is the usual requirement of a higher GHSV to obtain more $C_2+$ alcohols with concurrent decrease in carbon monoxide conversion.

SUMMARY OF THE INVENTION

The invention is a process for selectively producing mixed alcohols from synthesis gas comprising contacting a mixture of hydrogen and carbon monoxide with a catalytic amount of a catalyst wherein the catalyst is of components of (1) a catalytically active metal of molybdenum, tungsten or rhenium, in free or combined form;
(2) a co-catalytic metal of cobalt, nickel or iron, in free or combined form;
(3) a Fischer-Tropsch promoter; and
(4) an optional support;

said components combined by dry mixing, mixing as a wet paste, wet impregnation or if the first component is rhenium co-precipitation, and then sulfided, under conditions sufficient to form said product in at least 20 percent $CO_2$ free carbon selectivity.

The mixed alcohols produced find many known uses, such as use as a motor fuel or motor fuel additive, otherwise combustible fuels, solvents, and if further processed appropriately, antiseptics and other uses as known in the various arts.

It is a feature of this invention, that high yields and selectivity may be obtained without the use of rhodium, copper, ruthenium or zinc. An advantage of the invention is that high production rates may be obtained at high selectivities. Under preferred conditions, these catalysts may yield high $C_{1-5}$ alcohol productivity. Up to about 1.4 weight units $C_{1-5}$ alcohol/hr/weight unit of catalyst may be achieved. With cobalt, iron or nickel added to the catalyst the ratio of $C_1$ to $C_{2-5}$ alcohols may be considerably lower than for the same catalyst without the iron, nickel or cobalt, while still retaining the high catalyst activity and low sulfur level mixed alcohol fraction. Because of the high selectivity, complex purification steps may be avoided and the alcohol product may have a low acid content and have a high octane blending value. This may permit blending into motor fuels without elaborate processing. In addition, contrary to what is experienced with a molybdenum catalyst as one increases the temperature the ratio of $C_1$ to $C_{2-5}$ alcohols may stay the same or may even decrease.

The ease of catalyst preparation, simplicity and efficiency of control of the product mix are unique and advantageous in the process. Usually with increasing intimacy of contact between the catalytically active metal and the co-catalytic metal, at generally equivalent conditions of reaction, the weight ratio of higher alcohols to methanol produced increases; selectivity to mixed alcohols at high conversion increases; and the relative insensitivity to feed gas sulfide level increases.

The process is heterogeneously catalyzed. The process itself is extremely efficient in conversion of synthesis gas into mixed alcohols.

DETAILED DESCRIPTION OF THE INVENTION

The hydrogen and carbon monoxide required for this process can be obtained by methods known in the art. Examples are gasification of hydrocarbonaceous materials such as coal, high specific gravity oils, or natural gas; as a by-product of partial combustion cracking of hydrocarbons; by steam reforming of liquid or gaseous hydrocarbons; through the water-gas shift reaction; or some combination of these. The two components may also be generated separately and combined for the subject reaction.

The molar ratio of hydrogen to carbon monoxide in the feed gas which contacts the catalyst is such that the mixed alcohols are produced. Preferably, lower limits of the ratio are about 0.25, more preferably about 0.5 and most preferably about 0.7. Preferably, equivalent upper limits are about 100, more preferably about 5 and most preferably about 3. A most preferred range of from about 0.7 to about 1.2 holds for unsupported Fischer-Tropsch promoted sulfided Co/Mo catalysts.

Generally, the selectivity to alcohols is dependent on the pressure. Pressures are such that the mixed alcohols are produced. In the normal operating ranges, the higher the pressure at a given temperature, the more selective the process will be to alcohols. The minimum preferred pressure is about 500 psig (3.55 MPa). The more preferred minimum is about 750 psig (5.27 MPa) with about 1,000 psig (7.00 MPa) being a most preferred minimum. While about 1,500 psig (10.45 MPa) to about 4,000 psig (27.7 MPa) is the most desirable range, higher pressures may be used and are limited primarily by cost of the high pressure vessels, compressors and energy costs needed to carry out the higher pressure reactions. About 10,000 psig (69.1 MPa) is a typical preferred maximum with about 5,000 psig (34.6 MPa) a more preferred maximum. About 3,000 psig (20.8 MPa) is a most preferred pressure for the catalyst.

The selectivity to alcohols is also a function of temperature and is interrelated with the pressure function. Temperatures are such that the mixed alcohols are produced. However, the minimum temperature used is governed by productivity considerations and the fact that at temperatures below about 200° C., volatile catalytic metal carbonyls may form. Accordingly, the preferred minimum temperature is generally about 200° C. A preferred maximum temperature is about 400° C. A more preferred maximum is about 350° C. The most preferred range of operation is foom about 240° C. to about 325° C.

Alcohols herein are compounds otherwise hydrocarbons which contain at least one hydroxy functionality bound to carbon therein and generally does not include other compounds present such as esters or aldehydes. For example, the methanol portion of methyl acetate is not counted as methanol. Phenol is considered an alcohol herein. Mixed alcohols include $C_{1-10}$ alcohols. Preferred are $C_{1-5}$ mixed aliphatic alcohols. The mixed alcohol fraction usually formed using the aforementioned conditions may contain methanol, ethanol, 1-propanol, 2-propanol, 1-butanol, 2-butanol, 2-methyl-1-propanol, 2-methyl-2-propanol, other $C_{2-4}$ alcohols and $C_{5-10}$ alcohols. Preferably, the selectivity to $C_{2-5}$ aliphatic alcohols is high while the selectivity to methanol is low. The product mixture, as formed under preferred conditions, contains only small portions of other oxygenated compounds besides alcohols. These other compounds may not be deleterious to using the product, as is, in motor fuels.

In all cases, the mixed alcohol fraction is formed in at least about 20 percent $CO_2$ free carbon selectivity. Preferably, the alcohol fraction is formed in at least about 50 percent $CO_2$ free carbon selectivity, more preferably greater than about 70 percent and especially about 75 percent or more. Alcohols may be obtained in about an 85 percent $CO_2$ free carbon selectivity or more. Preferably, $CO_2$ free carbon selectivity to methanol is less than about one-half the $CO_2$ free carbon selectivity of the whole mixed alcohol fraction, more preferably about one-third or less and most preferably about one-fourth or less.

By percent $CO_2$ free carbon selectivity it is meant the percent of carbon in a specific product with respect to the total carbon converted from carbon monoxide to some product other than carbon dioxide or water. For example, one mole of ethyl alcohol is 2 moles of carbon and would represent 50 carbon mole percent selectivity to ethanol if 4 moles of CO were converted to products other than $CO_2$ and water. As conversion increases, the product distribution of mixed alcohols produced usually shifts toward higher molecular weight alcohols.

The process yields substantial quantities of alcohols. Under preferred conditions, the weight units per hour of alcohols boiling in the range of motor gasoline per weight unit of catalyst may exceed 0.2. Under certain conditions, it may exceed 1.0 and may reach 1.4.

The alcohol fraction formed at greater than a 20 percent $CO_2$ free carbon selectivity boils in the motor gasoline range. The minimum boiling pure alcohol is methanol at 64.7° C. ASTM D-439 calls for a 225° C. endpoint for automotive gasoline. Accordingly, the mixed alcohol fraction formed at greater than a 20 percent $CO_2$ free carbon selectivity may boil in the range of from about 60° C. to about 225° C. when distilled by ASTM D-86. Other alcohols may boil outside this range but preferably do not. It is not necessary that the entire liquid product boil in this range, but it is preferred. It is not necessary that the alcohol fraction meet all the distillation specifications for motor gasolines—only that it boil within the broad range of motor gasolines. For example, it need not be within 50 percent evaporated limits as set by ASTM D-439. Only 20 carbon mole percent of the total $CO_2$ free product must be alcohols that boil in this range. The alcohol fraction formed may be used as a motor fuel blending stock. Preferably, the alcohol fraction formed will have a research octane blending value in motor gasoline of greater than about 100, more preferably greater than about 110 and most preferably greater than about 120.

With the catalyst of the invention the $C_1$ to $C_{2-5}$ weight ratio may be less than one, preferably is less than about 0.8, more preferably less than about 0.5 and most preferably less than about 0.4 and can even be about 0.25 or lower. Primarily, the $C_{2-5}$ alcohol that increases is ethanol. The ethanol may be greater than 25 weight percent, preferably greater than 30 weight percent and most preferably greater than 40 weight percent of the $C_{1-5}$ alcohol fraction.

The ratio of $C_1$ to $C_{2+}$ alcohols means the weight ratio of methanol to higher alcohols such as ethanol, propanols, butanols, etc., taken as a whole. This number may be calculated by determining the weight fraction of methanol in the mixed alcohols. When the weight fraction of methanol is x, the ratio of $C_1$ to $C_{2+}$ alcohols is $x/(1-x)$. Since $C_{2+}$ alcohols, in its broadest definition refers to alcohols which are not detected by conventional analytical techniques, a more meaningful approximation of the $C_1$ to $C_{2+}$ ratio of methanol to higher alcohols includes only the $C_{2-5}$ alcohols in the definition of $C_{2+}$ alcohols. Alcohols bound as esters or ethers are not included in either the $C_1$ or $C_{2+}$ numbers.

Preferably, the co-products formed with the alcohol fraction are primarily gaseous products. That is $C_{1-4}$ hydrocarbons. Preferably, $C_{5+}$ hydrocarbons are co-produced at less than about 20 percent $CO_2$ free carbon selectivity, more preferably at less than 10 percent and most preferably at less than 5 percent. Lower amounts of normally liquid hydrocarbons make the normally liquid alcohols easier to separate from by-products.

Under preferred conditions, the amount of water formed is substantially less than the amount of alcohols formed. Typically there is less than about 20 weight percent and preferably less than about 10 weight percent water based on the quantity of alcohol. More preferably, the weight percent of water is about 5 or less, most preferably about 2 or less. This water may be removed by known techniques. If the water content is about 2 weight percent or less based on alcohols, the water may advantageously be removed by absorption on molecular sieves. At higher water contents, one may use a water gas shift drying step as disclosed in British Pat. Nos. 2,076,015 and 2,076,423 (hereby incorporated by reference). Use of a sulfur and molybdenum tolerant catalyst such as Haldor Topsoe SSK is preferred in the water gas shift drying step.

The $H_2$/CO gas hourly space velocity (GHSV) is a measure of the volume of hydrogen plus carbon monoxide gas at standard temperature and pressure passing a given volume of catalyst in an hour's time. GHSV is such that the mixed alcohols are produced. Preferably, lower limits of GHSV are about 100 hour$^{-1}$ and more preferably about 2,000 hour$^{-1}$. Preferably, equivalent upper limits are about 20,000 hour$^{-1}$ and more preferably about 5,000 hour$^{-1}$. Selectivity to the alcohols usually increases as the space velocity decreases. Conversion of carbon monoxide decreases as space velocity increases.

Preferably, at least a portion of the unconverted hydrogen and carbon monoxide in the effluent gas from the reaction, more preferably after removal of product alcohols, water and carbon dioxide formed and even more preferably any hydrocarbons formed, may be recycled to the reaction. The amount of recycle is expressed as the recycle ratio which is the ratio of moles of gases in the recycle stream to the moles of gases in the fresh feed stream. A recycle ratio of zero is within the scope of the invention with at least some recycle preferred. A recycle ratio of at least about one is more preferred and at least about three is most preferred.

With preferred catalysts and under preferred conditions of temperatures, pressures, $H_2/CO$ ratio, GHSV and recycle ratio, about 0.1 weight units of alcohols or more per hour may be formed per weight unit of catalyst. Under the more preferred conditions of about 310° C., 1500 psig (10.45 MPa), 3800 hour$^{-1}$ and a $H_2/CO$ ratio of about 1:1, with a 2Mo/Co catalyst, about 0.3 weight units of alcohol or more per hour per weight unit of catalyst may be obtained. Under the most preferred conditions of about 340° C., 3000 psig (20.9 MPa), a GHSV of 13,000 and a $H_2/CO$ ratio of 1.1; with a 2Mo/Co catalyst about 1.4 weight units of alcohols or more per hour per weight unit of catalyst may be obtained.

In addition, the synthesis should be carried out at as little feed conversion per pass as is compatible with economic constraints related to the separation of the alcohol product from unreacted feed and hydrocarbon gases. Accordingly, one would increase the space velocity and recycle ratios to preferably obtain about 15-25 percent conversion per pass.

The metal in the catalytically active metal may be of molybdenum (i.e., Mo), tungsten (i.e., W) and/or rhenium (i.e., Re). Mo and W are a more preferred group. Molybdenum is most preferred.

In the finished catalyst, the Mo, W or Re may be present in free of combined form. In free or combined form means the metal component at hand may be present as a metal, alloy or compound of the metal component. Representative compounds may include compounds used to prepare the finished catalyst.

In the case of Mo, W and Re, the sulfides, carbonyls, carbides and oxides are preferred in the finished catalyst. The sulfides are most preferred.

Typically, the catalytically active metal is generally present in the finished catalyst as the sulfide. It is not necessary for the practice of this invention that any particular stoichiometric metal sulfide be present, only that the metal sulfide is catalytically active itself for mixed alcohols production from synthesis gas before mixing with the co-catalytic metal and is generally present in combination with sulfur. Some of the catalytically active metal sulfide may be present in combination with other elements such as oxygen or as oxysulfides. The atomic ratio of sulfur to the metal in the catalytically active metal separately from the co-catalytic metal preferably has a lower limit of about 0.1 and more preferably a lower limit of about 1.8. Preferably, equivalent upper limits are about 3, more preferably about 2.3. Most preferably, the catalytically active metal comprises a catalytically active metal disulfide.

The catalytically active metal may be prepared by any known method. For example, agglomerated molybdenum sulfide catalysts may be made by thermal decomposition of ammonium tetrathiomolybdate or other,thiomolybdates as disclosed by Naumann et al., U.S. Pat. Nos. 4,243,553 and 4,243,554 (both hereby incorporated by reference), from purchased active molybdenum sulfides, or by calcining $MoS_3$. A preferred method of preparing catalytically active molybdenum sulfide is by decomposing ammonium tetrathiomolybdate that is formed by reacting a solution of ammonium heptamolybdate with ammonium sulfide followed by spray drying and calcining to form the molybdenum sulfide. Tungsten preparations are often similar. The addition of precipitating liquids, evaporation and cooling may be employed and may be advantageous with all catalyst metal components.

Representative molybdenum-, tungsten- or rhenium-containing compounds which may be used in preparing the catalyst include the sulfides, carbides, oxides, halides, nitrides, borides, salicylides, oxyhalides, carboxylates such as acetates, acetyl acetonates, oxalates, etc., carbonyls, and the like. Representative compounds also include the elements in anionic form such as molybdates, phosphomolybdates, tungstates, phosphotungstates, perrhenates and the like, and especially include the alkali, alkaline earth, rare earth and actinide series compounds of these anions.

The catalytically active metal may also be supported, but an unsupported catalytically active metal is preferred. By unsupported is meant that about 5 percent or less by weight of material, not a catalytically active metal, co-catalytic metal, binders or pelleting lubricants, are present in the finished catalyst. The unsupported catalytically active metal preferably has a surface area of at least 10 $m^2/g$ and more preferably more than 20 $m^2/g$ as measured by the BET nitrogen surface area.

The catalytically active metal may be present in an amount based on the weight of the total finished catalyst of at least about two percent, preferably at least about 5 percent with an upper limit of about 70 percent and more preferably about 30 percent of the total catalyst as if the metal disulfide. When supported, other materials would also have to be considered with respect to the fraction of catalyst that is the active metal, such as, agglomerating agents, binders, pelleting lubricants, promoters and other catalytic materials.

The catalyst contains a co-catalytic metal of cobalt (i.e., Co), nickel (i.e., Ni) or iron (i.e., Fe). A co-catalytic cobalt, nickel or iron compound herein is a cobalt, nickel or iron compound which enhances the catalytic properties of the finished sulfided catalyst as herein described. Cobalt and nickel are preferred. Cobalt is more preferred.

The co-catalytic metal may also be present in the finished catalyst in free or combined form. Representative co-catalytic compounds which may be used in preparing the catalyst and which may be present in the finished catalyst include the sulfides, carbides, oxides, halides, nitrides, borides, salicylides, oxyhalides, carboxylates such as acetates, acetyl acetonates, oxalates, etc., carbonyls, and the like. Representative compounds also include the co-catalytic elements combined with the catalytically active metal elements in anionic form such as iron, cobalt or nickel molybdates, phoshomolybdates, tungstates, phosphotungstates, perrhenates and the like. The sulfides, carbonyls, carbides and oxides are preferred in the finished catalyst with the sulfide being most preferred. Most preferably, some cobaltous species are present in the finished catalyst, especially the sulfide.

Examples of cobalt compounds which may be used in preparation of the catalyst, and which are preferred preparative cobalt compounds, are the following cobaltous compounds: the acetate tetrahydrate; orthoarsenate octahydrate; benzoate tetrahydrate; bromate hexahydrate; bromide; bromide hexahydrate; carbonate; basic carbonate; chlorate hexahydrate; perchlorate; perchlorate pentahydrate; perchlorate hexahydrate; chloride; chloride dihydrate; chloride hexahydrate; citrate dihydrate; cyanide dihydrate; cyanide trihydrate; ferrocyanide; ferrocyanide hydrates; fluoride; fluoride tetrahydrate; formate dihydrate; hydroxide; iodate; iodate hexahydrate; α-iodide; β-iodide; iodide dihydrate; iodide hexahydrate; linoleate; nitrate hexahydrate; oleate; oxalate; oxalate dihydrate; oxide; palmitate; orthophosphate; orthophosphate dihydrate; orthophosphate octahydrate; perrhenate pentahydrate; propionate trihydrate, selenate pentahydrate; selenate hexahydrate; selenate heptahydrate; selenide; sulfate; sulfate monohydride; sulfate hexahydrate; sulfate heptahydrate; sulfide; sulfite pentahydrate; tartrate; thiocyanate trihydrate; tungstate; and cobaltous complexes of the aforementioned cobaltous compounds and the like wherein ammonia, mono-, di-, tri-, tetra-, penta-, hexa-, and the like, amino compounds such as ethylamine, ethylenediamine, N,N'-dimethyl ethylenediamine and the like, phosphines, stibines, alcohols, ketones like acetone and the like, thio compounds, carboxylic acids, water, carbonyls, combinations of these as found in ethylenediamine tetraacetic acid, glycine, thiomorpholine and the like, are coordinated alone or in combination to the cobaltous compound. Cobaltic complexes and the like may be decomposed into a state comprising a cobaltous compound. The most preferred co-catalytic metal used in preparing the catalyst is cobaltous acetate tetrahydrate.

Most preferably, the co-catalytic metal used in preparation of the catalyst itself is not susceptible to oxidation in the ambient air at normal temperature and pressure (i.e., NTP, about 20° C.–30° C. and atmospheric pressure) and otherwise normal conditions (e.g., absence of proximate actinic radiation). Cobaltous sulfide is an example of a co-catalytic metal that is itself susceptible to oxidation in the ambient air. Also, strong oxidants are most preferably absent.

The iron, cobalt or nickel or mixtures thereof may be present in an amount based on the weight of the total catalyst of at least about 2 percent, preferably at least about 5 percent with an upper limit of about 70 percent and preferably about 30 percent of the total catalyst.

The Mo/W/Re and Co/Ni/Fe components may be present in the finished catalyst in an atomic ratio of about 1:10 to about 10:1. Preferably, they are present in a ratio of from about 1:4 to about 4:1.

The varied selectivity is based on a molar ratio of metal in the catalytically active metal to metal in the co-catalytic metal of from about 1:1 to about 3:1. With many preferred systems, the ratio is about 2:1.

The extent of intimate contact between the supported or unsupported catalytically active metal and the supported or unsupported co-catalytic metal is preferably achieved by dry mixing such as by repeated grinding and pressing, and powderizing by mechanical agitation and pressing as a finely divided powder, or by mixing the catalytically active metal and the co-catalytic metal with a liquid carrier such as by a wet paste or by wet impregnation. By this manner of mixing, the catalyst is air-stable outside the reactor, unlike catalysts such as a coprecipitated molybdenum sulfide/cobaltous acetate, which are usually susceptible to oxidation in ambient air due to the presence of cobaltous sulfide.

By intimate contact, it is meant that the catalytically active metal and the co-catalytic metal are in microscopic proximity to each other. Based on the stated molar ratio of metal in the catalytically active metal to metal in the co-catalytic metal, the higher the extent of intimate contact between the components (including promoter), the more selectivity to $C_{2+}$ alcohols, especially $C_{2-5}$ alcohols results; the more mixed alcohols at high conversion are produced; the more relatively insensitive the sulfided catalyst is to feed gas sulfide level; and the more equivalent the distribution of the $C_{2-5}$ alcohols, especially ethanol and n-(alkyl)alcohols, becomes. The lower the extent of intimate contact, the more the sulfided catalyst shows more selectivity to methanol; less mixed alcohols production; and more sensitivity to feed gas sulfide level. The sulfided catalyst can shift alcohols production to levels intermediate to these by selecting the extent of intimate contact.

Mixing as a paste and impregnation are preferred methods which achieve a very high extent of intimate contact between the catalytically active metal and the co-catalytic metal and are the upper bounds of this invention for Mo and W. Dry mixing can achieve a high extent of intimate contact to the extent that the dry mixing serves to distribute the catalytically active metal and the co-catalytic metal in microscopic proximity to each other. Dry mixing herein means mixing outside the presence of an added liquid carrier in which the mixed catalytic components are more than slightly soluble, preferably mixing substantially outside the presence of any liquid. Dry mixing is a more preferred upper limit, in large part due to the simplicity and ease in preparing the desired catalyst.

It is a preferred lower limit of the extent of intimate contact that the catalytic components be of particles the equivalent of 1 cm in diameter (to one significant figure) or less, and that these particles or the equivalent thereof be uniformly mixed. Examples of an equivalent to components being uniformly of such particle sizes would be an extended surface composed of, coated with or impregnated with, the catalytically active metal in intimate contact with such particles of co-catalytic metal and the Fischer-Tropsch promoter, or vice versa.

If the catalytically active metal, co-catalytic metal and a Fischer-Tropsch promoter are mixed in granular form without grinding or compaction to enhance the intimate contact, and sulfided (e.g., as in Example 1 herein), this granular catalyst produces mixed alcohol compositions which somewhat resemble the mixed alcohol compositions produced by Fischer-Tropsch promoted metal sulfide catalysts without an intimately mixed co-catalytic metal. However, this granular catalyst shows generally higher selectivity to mixed alcohols than does a generally comparable Fischer-Tropsch promoted catalytic metal, sulfided (e.g., as in Example 1 herein) catalyst alone.

Thus, the following are each additionally preferred lower limits of the extent of intimate contact of any component particles, especially particles of the catalytic metal and co-catalytic metal and promoter and most especially particles of the catalytic metal and co-catalytic metal: about 35 mesh or smaller; about 80 mesh or smaller; about 325 mesh or smaller; about 10 microns or less in diameter; about 2 microns or less in diameter; and about ½ micron or less in diameter, as desired. The smaller the particles, the higher the extent of intimate contact.

Mesh designations are Tyler designation herein. Thus, 35 mesh is about 420 microns.

The extent of intimate contact may be additionally enhanced by the application of pressure, such as pressing the components together in a press or by grinding in a mortar and pestle or in a milling operation and the like. The following are each additionally preferred lower limits of the variable enhancement of the extent of intimacy attained by the application of pressure: about 1000 psi or greater; about 5000 psi or greater; about 15,000 psi or greater; about 25,00 psi or greater, as desired. The higher the pressure, the higher the extent of intimate contact.

The duration of the application of pressure can affect the extent of intimate contact. Generally, as the time of the application of pressure is extended, the extent of intimate contact is enhanced. However, as the time period under pressure becomes increasingly long, no further appreciable effects may result.

The catalyst is promoted with a Fischer-Tropsch promoter, which characteristically increases the basicity of the catalyst. The following are exemplary: one or more of the alkali elements, alkaline earth elements, or smaller amounts of thorium in free or combined form. Alkali elements include lithium, sodium, potassium, rubidium and cesium. Alkaline earth elements include beryllium, magnesium, calcium, strontium and barium. Alkali and alkaline earth metals are preferred. Alkali metals are more preferred, and cesium and potassium are most preferred. Potassium is most preferred.

The Fischer-Tropsch promoter may be present in free or combined form. In free or combined form means that if the Fischer-Tropsch promoter is a metal, it is present as a metal, oxide, carbonate, hydroxide, sulfide, as a salt, in a compound with another component or a combination of these. The Fischer-Tropsch promoter is preferably present at a level sufficient to render the supported catalyst or the bulk catalyst more basic. The Fischer-Tropsch promoter is generally present in an amount of at least about 0.05 weight percent, with metal promoters calculated as if a free element in the finished catalyst. Preferably, it is present in an amount of at least about 0.5 percent and most preferably at least 2.0 percent. Large amounts, up to about 30 percent, of the Fischer-Tropsch promoter may be present. Preferably, it is present at less than 20 percent. The presence of the Fischer-Tropsch promoter shifts selectivity to $C_{2}+$ alcohols.

The Fischer-Tropsch promoter may be added as a ingredient to a catalytic component or to a support or may be part of one of the catalytic components such as sodium or potassium molybdate or as an integral part of the support. For example, carbon supports prepared from coconut shells often contain small amounts of alkali metal oxides or hydroxides or the support may contain a substantial amount of the Fischer-Tropsch promoter such as when the support is magnesia.

The Fischer-Tropsch promoter may be added to the active catalytic element prior to, during, or after the formation of the sulfide. For example, physical mixing or solution impregnation may be employed.

The catalyst may be combined with binders such as bentonite clay, and/or pelleting lubricants such as Sterotex ® and formed into shapes for use as a finished catalyst.

An optional component of the catalyst is a support which may assume any physical form such as pellets, granules, beads, extrudates, etc. The supports may be coprecipitated with the active metal species, or the support in powder form may be treated with the catalytic metal species and then used as is or formed into the aforementioned shapes, or the support may be formed into the aforementioned shapes and then treated with the catalytic species.

The catalytic species may be dispersed on the support by methods known in the art. Examples include impregnation from solution followed by conversion to the sulfided species or intimate physical mixing. One or more of these methods may be used. Preferred methods of placing molybdenum sulfide on a support are impregnation with aqueous ammonium tetrathiomolybdate followed by thermal decomposition to the sulfide or in situ formation of the sulfide by contacting of soluble molybdenum and a soluble sulfide in the presence of the support. The former is more preferred. The catalytic species may be dispersed on separate supports and then intimately contacted.

The exemplary support materials include: the aluminas, basic oxides, the silicas, carbons, or suitable solid compounds of magnesium, calcium, strontium, barium, scandium, yttrium, lanthanum and the rare earths, titanium, zirconium, hafnium, vanadium, niobium, tantalum, thorium, uranium, and zinc, of which oxides are exemplary compounds. Preferably, the supports are neutral or basic or may be rendered neutral or basic by addition of the alkaline promoters. The aluminas include the alpha, gamma, and eta types. The silicas include, for example, silica gel, diatomaceous earth, and crystalline silicates.

The carbon supports, which are preferred supports, include activated carbons such as those prepared from coals and coal-like materials, petroleum-derived carbons and animal- and vegetable-derived carbons. Preferably, the carbon support will have a surface area of $1-1500$ $m^2/g$, more preferably $10-1000$ $m^2/g$ and most preferably $100-500$ $m^2/g$ as measured by the BET nitrogen test. Preferably, micropores ($<20$ Angstroms) are minimized and at least 20 percent of the volume of the pores is comprised of pores having a diameter of from about 20 Angstroms to about 600 Angstroms. Examples may include coconut shell charcoal, coals, petroleum cokes, carbons formed by pyrolyzing materials such as vinylidene chloride polymer beads, coal, petroleum coke, lignite, bones, wood, lignin, nut shells, petroleum residues, charcoals, etc.

Based upon the weight of the total sulfided catalyst, the support when present generally comprises from about 20 weight percent or more of the catalyst and about 96 weight percent or less of the catalyst. Preferably, the support when present comprises about 50 weight percent or more and most preferably about 70 weight percent or less of the sulfided catalyst.

Catalysts of the invention preferably contain less than 25 weight percent, based on the total weight of carbon oxide hydrogenation active metals, of other carbon oxide hydrogenation active metals and more preferably less than 20 weight percent and most preferably less than 2 weight percent. The inventive catalyst may be essentially free of other carbon oxide hydrogenating components. By essentially free it is meant that other carbon oxide hydrogenating components do not significantly alter the character or quantity of the alcohol fraction. For example, a significant change would be a 5 percent change in the amount of the alcohol fraction or a 5 percent change in the percentage of any alcohol in the alcohol fraction.

Carbon oxide hydrogenating components present in thus limited quantities or excluded are preferably those that contain chromium, manganese, copper, zinc, ruthenium and rhodium. More preferably, in addition to the above-mentioned components, those that are excluded contain halogen, titanium, vanadium, cerium, thorium, uranium, iridium, palladium, platinum, silver or cadmium.

The catalyst is then sulfided. Sulfiding may be accomplished by first treating with flowing hydrogen at elevated temperatures followed by a mixture of hydrogen and hydrogen sulfide. Temperatures may be elevated periodically in a stepwise function.

The finished catalyst may be used as its final form admits in a fixed bed, moving bed, fluid bed, ebullated bed or a graded bed wherein concentration and/or activity of the catalyst varies from inlet to outlet in similar manner to known catalysts. The catalyst may be used in powdered form or formed into a shape with or without binders.

The catalysts of the invention may be employed individually or in combination with other inventive catalysts or with other previously proposed catalysts and activators for the claimed process.

Under preferred reaction conditions the catalyst may be stable and active for as many as 6000 hours or more. Activity and selectivity are preferably substantially retained after 700 hours of operation, more preferably after 2000 hours and most preferably after 4000 hours operation.

Reduced oxide catalysts may generally be regenerated by reduction with hydrogen. After this, the catalyst may regain selectivity and most of its original activity and be used for another long period of time before regenerating again.

The catalysts are generally not adversely affected by up to 100 ppm sulfur in the $H_2$/CO feed. However, no advantage is realized by the presence of sulfur, and generally sulfur must be removed from the mixed alcohols fraction. Accordingly, low sulfur levels in the feed are preferred.

COMPARATIVE EMBODIMENTS

In the general method of these comparisons, the catalysts are prepared as follows in Comparisons A–G. The reactor consists of a one-half inch (1.27 cm) stainless steel tube packed with catalyst. The total volume of catalyst is about 6 cm$^3$. Premixed hydrogen, carbon monoxide, and nitrogen feed gases from cylinders are compressed and regulated at the pressures stated in the table. The feed gas mixture consists of hydrogen and carbon monoxide at the stated molar ratios and about 5 percent by volume of nitrogen serving as an internal standard. About 50 ppm of $H_2S$ is also present in the feed gas.

The mixed feed gas passes through the bed of activated carbon at room temperature to remove iron and other carbonyl contaminants. The feed gas then passes at the stated hourly space velocities through the fixed bed reactor which is maintained at the stated reaction temperatures by an electric air recirculated oven and which is held at 1500 psig (10.45 MPa . The reactor effluent passes through a gas liquid separator at ambient temperature and the reaction pressure stated in series with a dry ice trap at ambient pressure. Both gas and liquid phases are analyzed to give the results in Table I.

CATALYSTS

Comparison A

A solution of 180 g of $(NH_4)_6Mo_7O_{24}.4H_2O$ in 500 cm$^3$ of water containing 100 cm$^3$ of concentrated $NH_4OH$ reacts with a small excess of $(NH_4)_2S$ (about 1300 cm$^3$ of 22 percent $(NH_4)_2S$ in water). The reaction mixture is stirred at 60° C. for one hour and evaporated to dryness at 60° C.–70° C. A portion of the resulting $(NH_4)_2MoS_4$ is calcined at 500° C. for one hour in an inert atmosphere such as nitrogen to form $MoS_2$. The resulting $MoS_2$ powder (6.6 g) is mixed with 2.0 g of bentonite clay, 1.0 g of $K_2CO_3$ and 0.4 g of a pelleting lubricant (Sterotex®)by grinding in a mortar and pestle. The product is used to make alcohols in the unpelleted powder state. No pretreatment of the catalyst is performed.

Comparison B

A 10.0-g portion of the $MoS_2$ from Comparison A is mixed in a mortar and pestle with 8.4 g of $Co(CH_3CO_2)_2.4H_2O$ (cobalt acetate) and water sufficient to yield a thick paste. The paste is dried at 60° C. and calcined at 500° C. for one hour in an inert gas such as nitrogen to give a black powder with a Mo/Co atomic ratio of about 3:1.

Similar to Comparison A, 6.6 g of this powder is mixed with 2.0 g bentonite clay, 1.0 g of $K_2CO_3$ and 0.4 g of Sterotex® in a mortar and pestle. This catalyst is used in unpelleted powder form and is not pretreated.

Comparison C

A coprecipitated cobalt/molybdenum sulfide is prepared with a Mo/Co atomic ratio of about 2:1. Fifteen grams of $(NH_4)_6Mo_7O_{24}.4H_2O$ (0.085 mole Mo) is dissolved in 106 cm$^3$ of 22 percent $(NH_4)_2S$ in water and stirred at 60° C. for one hour to form $(NH_4)_2MoS_4$. A solution of 10.5 g of $Co(CH_3CO_2)_2$ (0.042 mole Co) is 200 cm$^3$ of water is prepared.

The two solutions are added simultaneously, dropwise to a stirred solution of 30 percent aqueous acetic acid in a baffled flask at 50° C. over a one-hour period. After stirring for one additional hour the reaction mix is filtered and the filter cake dried at room temperature and then calcined for one hour at 500° C. in an inert atmosphere such as nitrogen. Similar to Comparison B, 6.6 g of the calcined cobalt/molybdenum sulfide is ground together with 2.0 g of bentonite clay, 1.0 g of $K_2CO_3$ and 0.4 g of Sterotex® lubricant in a mortar and pestle. This catalyst is used in unpelleted, powder form without pretreatment.

Comparison D

This comparison discloses the making of a coprecipitated cobalt/molybdenum sulfide with a Mo/Co atomic ratio of about 3:1.

The coprecipitated cobalt/molybdenum sulfide is prepared using the same procedure as Comparison C except that 7.1 g of $Co(CH_3CO_2)_2.4H_2O$ (0.28 mole Co) is used. This catalyst is used in unpelleted, powder form without pretreatment.

Comparison E

This comparison discloses the use of a commercially available alkalized molybdenum/cobalt catalyst, Haldor Topsoe SSK, and available from Haldor Topsoe A/S of Denmark.

Comparison F

This comparison discloses the use of an alkalized Mo/Ni sulfide having a Mo/Ni atomic ratio of about 2:1.

Seventy-five grams (0.425 mole) of $(NH_4)_6Mo_7O_{24} \cdot 4H_2O$ is dissolved in 530 cm$^3$ of 22 percent aqueous $(NH_4)_2S$ at 60° C.–70° C. with stirring for one hour to give a solution of $(NH_4)_2MoS_4$. A second solution containing 53 g of nickel acetate (0.212 mole Ni) in 500 cm$^3$ of water is prepared. These two solutions are added dropwise over a 40-minute period to one liter of vigorously stirred 30 percent acetic acid. After stirring for one additional hour at 60° C., the resulting slurry is filtered. The black filter cake is washed with water and dried overnight at 100° C. under nitrogen. The dry filter cake is calcined under nitrogen at 500° C. for one hour. Similarly to Comparison A, 6.6 g of the calcined Mo/Ni sulfide is ground with mortar and pestle with 2 g of bentonite clay, 1 g of $K_2CO_3$ and 0.4 g of Sterotex ® pelleting lubricant. The catalyst is used in unpelleted powder form without pretreatment.

Comparison G

This comparison discloses the use of a Mo/Fe sulfide made by coprecipitation.

A barium acetate solution, prepared by dissolving 12.2 g 0.071 mole) of $Ba(OH)_2$ in 100 cm$^3$ of water containing 10 cm$^3$ of glacial acetic acid, is mixed with 100 cm$^3$ of aqueous solution containing 19.7 g (0.071 mole) of $FeSO_4$. The resulting precipitate was filtered off under nitrogen and discarded, leaving a solution of ferrous acetate. A solution of $(NH_4)_2MoS_4$ (0.142 mole) is prepared by dissolving 25 g of $(NH_4)_2Mo_7O_{24} \cdot 4H_2O$ in 180 cm$^3$ of 22 percent aqueous $(NH_4)_2S$ and stirring at 60° C. for one hour. The solutions of ferrous acetate and ammonium tetrathiomolybdate are added simultaneously over a 30-minute period to a vigorously stirred solution of 75 cm$^3$ of glacial acetic acid in 225 cm$^3$ of water at 60° C. The resulting black slurry is stirred at 60° C. for one hour and filtered. The black filter cake is washed, dried at 110° C. overnight under nitrogen, and calcined at 500° C. under nitrogen for one hour. The calcined Mo/Fe sulfide is blended in a mortar and pestle with bentonite clay, $K_2CO_3$ and Sterotex ® to give a formulation containing 66 percent Mo/Fe sulfide, 20 percent clay, 10 percent $K_2CO_3$ and 4 percent Sterotex ®. This catalyst (5 cm$^3$) is combined with 5 cm$^3$ of tabular alumina and loaded into the reactor.

TABLE I

| Example | A | B | C | D | E | F | G |
|---|---|---|---|---|---|---|---|
| Temp. (°C.) | 265 | 295 | 305 | 295 | 350 | 300 | 321 |
| H$_2$/CO (molar ratio) | 1.04 | 0.98 | 0.98 | 0.98 | 1.02 | 1.03 | 1.04 |
| GHSV (hr$^{-1}$) | 1200 | 2200 | 1300 | 1050 | 614 | 1330 | 1480 |
| CO Conversion (%) | 33.1 | 10.3 | 39.0 | 29.2 | 12.7 | 33.1 | 27.1 |
| Wt. Units CO converted per wt. unit of catalyst per hour | 0.19 | 0.12 | 0.23 | 0.13 | 0.04 | 0.26 | 0.27 |
| CO$_2$ produced[1] (%) | 31.3 | 18.6 | 33.5 | 31.3 | 40.1 | 32.9 | 36.9 |
| Selectivities[2] (%) | | | | | | | |
| GAS PHASE | | | | | | | |
| CH$_4$ | 20.2 | 7.0 | 12.6 | 11.3 | 21.7 | 18.0 | 7.4 |
| C$_2$+ hydrocarbons | 4.3 | 3.2 | 5.7 | 3.2 | 4.9 | 2.7 | 16.4 |
| Subtotal | 24.5 | 10.2 | 18.2 | 14.5 | 26.6 | 20.7 | 24.1 |
| LIQUID PHASE | | | | | | | |
| Methanol | 32.3 | 37.8 | 16.1 | 22.7 | 17.7 | 15.2 | 6.9 |
| Ethanol | 31.8 | 29.5 | 39.9 | 40.7 | 15.2 | 41.8 | 21.0 |
| Propanols | 7.7 | 7.8 | 14.9 | 12.7 | 16.7 | 11.5 | 17.9 |
| Butanols | 1.6 | 5.3 | 4.3 | 3.5 | 10.9 | 1.4 | 10.8 |
| Pentanols | 0.2 | 2.4 | 0.5 | 1.2 | 5.0 | 1.5 | 7.1 |
| Subtotal | 73.6 | 82.8 | 75.7 | 80.8 | 65.5 | 71.4 | 63.7 |
| Weight Ratio C$_1$/C$_{2-5}$ alcohols | 1.13 | 1.24 | 0.39 | 0.57 | 0.60 | 0.39 | 0.19 |
| Other oxygenates[3] and hydrocarbons | 1.9 | 7.0 | 6.0 | 4.7 | 7.9 | 7.9 | 12.2 |
| H$_2$O[4] (wt. %) | 2.7 | 1.4 | 1.8 | 2.3 | 4.6 | 1.9 | 6.7 |

[1]100 × moles of CO$_2$ formed for each mole of CO converted in the reactor.
[2]Selectivities, except for CO$_2$, are based on carbon mole selectivity on a CO$_2$ free basis.
[3]Assumed a carbon number of 4 for other oxygenates.
[4]Water is calculated as weight percent of the liquid phase.

Specific Embodiments

The following examples and comparisons therein are illustrative of the invention. The compounds are of reagent grade or higher purity unless otherwise specified. Catalytic grade compounds are examples of such a higher purity grade. The syngas consists of 95 mole percent of CO plus H$_2$, 5 mole percent of N$_2$ and 50 ppm of H$_2$S.

The catalysts are loaded into the ½-inch internal diameter reactors like in the comparative embodiments and are sulfided before being used. The reactors are then brought to operating temperature in the presence of the feed gas. Next, feed from a high pressure gas bottle containing the syngas is allowed to flow through the manifold to the reactor like in the comparative embodiments. Pressure, flow and temperature are adjusted to operating values. Product analyses are reported in percent CO$_2$ free carbon selectivity, unless otherwise noted.

EXAMPLE 1

This is an example of the effect of the extent of intimate contact between a sulfided catalyst of a catalytically active metal and a co-catalytic metal. The effect of the presence of a co-catalytic compound is also shown.

The following components are intimately contacted by uniform dry mixing without liquid carrier as minus 35 to plus 45 mesh particles, without additional enhancement of the extent of intimate contact by pressure, for the indicated runs:

Runs a & b: 4.88 g $MoS_2$; 3.80 g $Co(O_2CCH_3)_2 \cdot 4H_2O$; 1.32 g $K_2CO_3$ Run c (comparative): 7.87 g $MoS_2$; 2.13 g $K_2CO_3$ After loading 5 cc of the non-sulfided composition in the reactor, each are sulfided according to the following procedure which is a simulation of pre-sulfiding techniques used commercially. The catalyst is purged with $H_2$ at 30 psig, flow rate of 50 hours$^-$ and room temperature for 1 hour. The temperature is increased to 170° C. and the pressure is increased to 55 psig and maintained for ½ hour. $H_2$ flow is shut off. A flow of $H_2+3$ percent $H_2S$ is started at 350 psig, flow rate of 100 hours$^{-1}$. The temperature is increased to 320° C. in 30° increments every ½ hour. This is held at 320° C. for ½ hour. The temperature is then reduced to 270° C. and the catalyst is exposed to the syngas. Under the following conditions, the following is observed:

|  | 1a | 1b | 1c |
| --- | --- | --- | --- |
| Time onstream (hours) | 186 | 260 | 187 |
| Temperature (°C.) | 307 | 309 | 307 |
| Pressure (psig) | 1435 | 1437 | 1430 |
| $H_2$/CO molar ratio | 1.06 | 1.06 | 1.06 |
| GHSV (hours) | 651 | 2529 | 572 |
| Recycle ratio | 0 | 0 | 0 |
| CO Conversion (%) | 42.6 | 14.4 | 46.5 |
| $CO_2$ produced (%) | 31.4 | 23.2 | 39.8 |
| GAS PHASE | | | |
| $CH_4$ | 14.2 | 7.6 | 28.4 |
| $C_2+$ hydrocarbons | 1.5 | 0 | 6.5 |
| Subtotal | 15.7 | 7.6 | 34.9 |
| LIQUID PHASE | | | |
| Methanol | 27.0 | 45.6 | 11.5 |
| Ethanol | 27.3 | 26.3 | 11.8 |
| Propanols | 11.8 | 6.3 | 19.6 |
| Butanols | 6.2 | 3.4 | 9.3 |
| Pentanols | 0.1 | 0 | 1.9 |
| Subtotal | 72.4 | 81.6 | 54.1 |
| Other oxygenates and hydrocarbons | 11.7 | 10.8 | 11.0 |
| $C_1/C_2+$ wt ratio | 0.70 | 1.40 | 0.34 |
| $H_2O$ (wt %) | 1.7 | 1.3 | 3.6 |

EXAMPLE 2

This is an example of a bulk catalytically active metal to which a co-catalytic metal is added by intimate mixing of the components by dry grinding.

The following components are intimately mixed by repeated physical grinding in mortar and pestle:
- 5.56 g $MoS_2$ (Climax Molybdenum, Lot 1038 HL)
- 4.34 g $Co(O_2CCH_3)_2 \cdot 4H_2O$
- 3.00 g Bentonite Clay
- 0.60 g Sterotex
- 1.50 g $K_2CO_3$ Using a Carver Press, the powder is compressed at 22,000 pounds force in a 1-inch diameter die (28,000 psi) to give wafers which are then ground to $-12+20$ mesh particles.

After loading 5 cc of the non-sulfided composition in the reactor, it is sulfided according to the procedure of Example 1. Under the following conditions, the following is observed:

|  | 2a | 2b | 2c |
| --- | --- | --- | --- |
| Time onstream (hours) | 48 | 165 | 209 |
| Temperature (°C.) | 281 | 302 | 328 |
| Pressure (psig) | 1493 | 1485 | 1492 |
| $H_2$/CO molar ratio | 1.09 | 1.13 | 1.12 |
| GHSV (hours) | 404 | 1242 | 3137 |
| Recycle ratio | 0 | 0 | 0 |
| CO Conversion (%) | 24.8 | 19.5 | 24.2 |
| Wt unit CO converted per wt unit of catalyst/hr | 0.061 | 0.144 | 0.451 |
| $CO_2$ produced (%) | 30.3 | 30.8 | 28.9 |
| GAS PHASE | | | |
| $CH_4$ | 10.2 | 10.2 | 11.4 |
| $C_2+$ hydrocarbons | 0.5 | 0 | 0.4 |
| Subtotal | 10.7 | 10.2 | 11.8 |
| LIQUID PHASE | | | |
| Methanol | 18.8 | 29.5 | 37.6 |
| Ethanol | 44.1 | 31.9 | 24.6 |
| Propanols | 7.0 | 6.8 | 9.3 |
| Butanols | 4.7 | 6.1 | 6.1 |
| Pentanols | 0 | 0 | 0 |
| Subtotal | 74.6 | 74.3 | 77.6 |
| Other oxygenates and hydrocarbons | 14.6 | 15.4 | 10.6 |
| $C_1/C_2+$ wt ratio | 0.38 | 0.71 | 1.09 |
| $H_2O$ (wt %) | 1.4 | 1.6 | 1.5 |

EXAMPLE 3

This is an example of a bulk catalytically active metal into which a co-catalytic metal is physically blended using a wet paste prior to sulfiding in the reactor.

A paste consisting of 10.0 g of catalytically active $MoS_2$ supplied by Climax Molybdenum Co., 7.8 g of $Co(O_2CCH_3)_2 \cdot 4H_2O$ and 10 ml of deionized water is repeatedly ground in a mortar and pestle. The paste is heated in $N_2$ at 2° C./minute to 300° C. where the temperature is held for 1 hour. The dry material is ground to powder. A mixture of 6.6 g of the powder, 2.0 g of Bentonite clay, 2.6 g of $Cs_2CO_3$ and 0.4 g of Sterotex is ground in a mortar and pestle then pressed into 1-inch (2.54 cm) diameter wafers at 28,000 psi. The pressed wafers are broken up and sieved to give 5.0 cc of $-12+20$ mesh catalyst.

The non-sulfided composition is treated in flowing $H_2+3$ percent $H_2S$ for 2 hours at 380° C. prior to exposure to syngas feed. After 382 hours onstream, the catalyst is treated in flowing $H_2$ at 500° C. for 2 hours then exposed to flowing $H_2+3$ percent $H_2S$ at 400° C. for 2 hours. The syngas feed is again turned on, and under the following conditions, the following is observed:

|  | 3a | 3b |
| --- | --- | --- |
| Time onstream (total hours) | 431 | 571 |
| Temperature (°C.) | 318 | 340 |
| Pressure (psig) | 1470 | 1413 |
| $H_2$/CO molar ratio | 1.11 | 1.12 |
| GHSV (hours) | 751 | 1968 |
| Recycle ratio | 0 | 0 |
| CO Conversion (%) | 25.1 | 20.9 |
| Wt unit CO converted per wt unit of catalyst/hr | 0.101 | 0.221 |
| $CO_2$ produced (%) | 33.0 | 31.1 |
| GAS PHASE | | |
| $CH_4$ | 14.5 | 15.3 |
| $C_2+$ hydrocarbons | 1.8 | 1.6 |
| Subtotal | 16.3 | 16.9 |
| LIQUID PHASE | | |
| Methanol | 20.6 | 27.5 |
| Ethanol | 42.4 | 36.2 |
| Propanols | 9.2 | 9.6 |
| Butanols | 3.8 | 3.5 |
| Pentanols | 0 | 0 |
| Subtotal | 76.0 | 76.8 |
| Other oxygenates and hydrocarbons | 7.9 | 6.4 |
| $C_1/C_2+$ wt ratio | 0.47 | 0.75 |

-continued

|  | 3a | 3b |
|---|---|---|
| $H_2O$ (wt %) | 2.5 | 2.6 |

EXAMPLE 4

This is an example of supported catalytically active metal onto which a co-catalytic metal is impregnated prior to sulfiding in the reactor.

A solution, heated to 50° C.-60? C., consisting of 1 part by weight of $K_2CO_3$, 5 parts by weight of $(NH_4)_6Mo_7O_{24}.4H_2O$ and 30 parts by weight of aqueous 22 percent $(NH_4)_2S$ is used in each of four impregnations of 189.9 g of pelleted 4-6 mesh MBV activated carbon (Witco Chemical Company). The hot solution is added dropwise to the carbon until the carbon is saturated. Solution volumes of 283, 220, 172 and 140 ml are absorbed by the carbon on successive impregnations. Following each impregnation, the wet composition is air-dried at room temperature until the carbon no longer appears wet. It is then heated in flowing nitrogen at a temperature increasing by 2° C./minute until 300° C. is reached. The 300° C. temperature is held for 1 hour.

A hot solution consisting of 1.3 g of $Co(O_2CCH_3)_2.4H_2O$ dissolved in 5 ml of deionized water is added dropwise over 5.2 g of a $-20+20$ mesh sample of the supported molybdenum sulfide catalyst. After air-drying at room temperature for a few hours, the impregnated composition is heated in flowing nitrogen at a temperature increasing by 2° C./minute until 300° C. is reached. The 300° C. temperature is held for 1 hour.

The nitrogen treated impregnated composition is treated in flowing $H_2+3$ percent $H_2S$ for 2 hours at 380° C. prior to exposure to syngas feed. After 382 hours onstream, the catalyst is treated in flowing $H_2$ at 500° C. for 2 hours then exposed to flowing $H_2+3$ percent $H_2S$ at 400° C. for 2 hours. Under the following conditions, the following is observed:

|  | 4a | 4b |
|---|---|---|
| Time onstream (hours) | 428 | 571 |
| Temperature (°C.) | 318 | 340 |
| Pressure (psig) | 1472 | 1428 |
| $H_2/CO$ molar ratio | 1.11 | 1.12 |
| GHSV (hours) | 1455 | 5650 |
| Recycle ratio | 0 | 0 |
| CO Conversion (%) | 27.3 | 14.8 |
| Wt unit CO converted per wt unit of catalyst/hr | 0.308 | 0.650 |
| $CO_2$ produced (%) | 40.7 | 36.0 |
| GAS PHASE |  |  |
| $CH_4$ | 15.5 | 14.7 |
| $C_2+$ hydrocarbons | 23.9 | 14.3 |
| Subtotal | 39.4 | 29.0 |
| LIQUID PHASE |  |  |
| Methanol | 13.1 | 24.4 |
| Ethanol | 24.7 | 27.4 |
| Propanols | 14.2 | 12.0 |
| Butanols | 5.8 | 3.8 |
| Pentanols | 1.2 | 0 |
| Subtotal | 59.0 | 67.6 |
| Other oxygenates and hydrocarbons | 1.6 | 3.4 |
| $C_1/C_2+$ wt ratio | 0.42 | 0.81 |
| $H_2O$ (wt %) | 5.9 | 5.8 |

EXAMPLE 5

Comparative: 5.4g of $ReS_2$ and 0.5 g of $K_2CO_3$ are ground with a mortar and pestle and loaded into the reactor. Under conditions of 290° C., 1450 psig, GHSV of 4000 $hr^{-1}$ and $H_2/CO$ molar ratio of 1, the $C_{1-5}$ alcohols selectivity is 40 percent with 70 percent of it methanol and 17 percent ethanol. Ten weight percent $H_2O$ is produced.

Invention: 5 g of $ReS_2$, 0.5 g of $K_2CO_3$ and 4 g of $Co(O_2CCH_3)_2.4H_2O$ are ground together with a mortar and pestle. Five cc of this mixture is loaded into the reactor and sulfided according to Example 1. If the catalyst is exposed to syngas under the comparative conditions of this example, ethanol selectivity improves.

The examples show some typical behavior of the catalyst of the invention having varied extents of intimate contact between the catalytically active metal and co-catalytic metal in the process of the invention.

I claim:

1. A process for selectively producing mixed alcohols from synthesis gas comprising contacting a mixture of hydrogen and carbon monoxide with a catalytic amount of a catalyst containing components of
   (1) a catalytically active metal of molybdenum, in free or combined form;
   (2) a co-catalytic metal of iron, in free or combined form; and
   (3) a Fischer-Tropsch promoter of an alkali or alkaline earth series metal, in free or combined form;
said components combined by dry mixing, mixing as a wet paste or wet impregnation, and then sulfided, said catalyst excluding rhodium, ruthenium and copper; at a pressure of at least about 500 psig and under conditions sufficient to form said mixed alcohols in at least 50 percent $CO_2$ free carbon selectivity, said mixed alcohols containing a $C_1$ to $C_{2-5}$ alcohol weight ratio of less than about 1:1.

2. The process of claim 1 wherein an extent of intimate contact is selected from the lower extent afforded by particles of the catalytically active metal and the co-catalytic metal being of a size about 35 mesh or smaller to a higher extent afforded by mixing as a wet paste or impregnation.

3. The process of claim 2 wherein the components are combined by dry mixing.

4. The process of claim 3 wherein the dry mixing is done substantially outside the presence of any liquid.

5. The process of claim 4 wherein the extent of intimate contact is additionally varied in the presence of pressure.

6. The process of claim 5 wherein the co-catalytic metal used in preparation of the catalyst is not susceptible to oxidation in ambient air at NTP and otherwise normal conditions.

7. The process of claim 6 wherein the promoter is present in amounts from about 0.05 weight percent to about 20 weight percent, calculated as if a free element in the finished catalyst.

8. The process of claim 7 wherein the Fischer-Tropsch promoter is an alkali metal, in free or combined form.

9. The process of claim 8 wherein the Fischer-Tropsch promoter is potassium, in free or combined form.

10. The process of claim 4 wherein the mixed alcohols are produced in at least 70 percent $CO_2$ free carbon selectivity.

11. The process of claim 10 wherein the mixed alcohols are produced in about a 75 percent or greater $CO_2$ carbon selectivity.

12. The process of claim 11 wherein the Fischer-Tropsch promoter is potassium, in free or combined form.

* * * * *